(12) United States Patent
Seyler

(10) Patent No.: US 10,092,461 B2
(45) Date of Patent: *Oct. 9, 2018

(54) THREE-DIMENSIONAL APERTURED FILM FOR TRANSMITTING DYNAMICALLY-DEPOSITED AND STATICALLY-RETAINED FLUIDS

(71) Applicant: Tredegar Film Products Corporation, Richmond, VA (US)

(72) Inventor: Rickey J. Seyler, Chesterfield, PA (US)

(73) Assignee: TREDEGAR FILM PRODUCTS CORPORATION, Richmond, VA (US)

(*) Notice: Subject to any disclaimer, the term of this patent is extended or adjusted under 35 U.S.C. 154(b) by 58 days.

This patent is subject to a terminal disclaimer.

(21) Appl. No.: 14/203,446

(22) Filed: Mar. 10, 2014

(65) Prior Publication Data

US 2014/0303585 A1 Oct. 9, 2014

Related U.S. Application Data

(63) Continuation of application No. 12/462,565, filed on Aug. 4, 2009, now Pat. No. 8,674,171, which is a continuation-in-part of application No. 12/316,323, filed on Jan. 29, 2009, now Pat. No. 8,415,524, which is a continuation of application No. 11/559,301, filed on Nov. 14, 2006, now Pat. No. 7,518,032.

(51) Int. Cl.
*A61F 13/15* (2006.01)
*A61F 13/20* (2006.01)
*A61F 13/537* (2006.01)

(52) U.S. Cl.
CPC .. *A61F 13/53713* (2013.01); *A61F 13/53747* (2013.01); *A61F 2013/53721* (2013.01); *A61F 2013/53782* (2013.01); *Y10T 428/24281* (2015.01)

(58) Field of Classification Search
USPC ............... 604/378, 383, 385.01, 385.101
See application file for complete search history.

(56) References Cited

U.S. PATENT DOCUMENTS 3,097,787 A 7/1963 Schur
3,945,386 A 3/1976 Anczurowski et al.
(Continued)

FOREIGN PATENT DOCUMENTS

EP 0761190 A1 3/1997
EP 1064892 A2 1/2001
(Continued)

OTHER PUBLICATIONS

Indian Office Action dated Jan. 16, 2017, for Indian Patent Application No. 1190/KOL/2007.

*Primary Examiner* — Michele M Kidwell
(74) *Attorney, Agent, or Firm* — Karceski IP Law, PLLC

(57) ABSTRACT

A three-dimensional film for use as a transfer layer in an absorbent article has a continuous surface and a discontinuous surface disposed generally parallel to and spaced from said continuous surface; both the continuous surface and the discontinuous surface have large scale apertures defined by sidewalls originating on the surface and extending outwardly therefrom and sized to permit acquisition of fluids by gravity, and optionally each surface also includes small scale apertures sized to acquire fluids by capillary action.

14 Claims, 3 Drawing Sheets

(56) References Cited

U.S. PATENT DOCUMENTS

| | | | |
|---|---|---|---|
| 3,967,623 A | 7/1976 | Butterworth et al. | |
| 4,323,069 A | 4/1982 | Ahr et al. | |
| 4,324,247 A | 4/1982 | Aziz | |
| 4,609,518 A | 9/1986 | Curro et al. | |
| 4,626,254 A | 12/1986 | Widlund et al. | |
| 4,637,819 A | 1/1987 | Ouellette et al. | |
| 4,726,976 A | 2/1988 | Karami et al. | |
| 5,078,710 A | 1/1992 | Suda et al. | |
| 5,158,819 A | 10/1992 | Goodman et al. | |
| 5,171,238 A | 12/1992 | Kajander | |
| 5,342,334 A | 8/1994 | Thompson et al. | |
| 5,352,217 A | 10/1994 | Curro | |
| 5,368,909 A | 11/1994 | Langdon et al. | |
| 5,368,910 A | 11/1994 | Langdon | |
| 5,387,209 A | 2/1995 | Yamamoto et al. | |
| 5,439,458 A | 8/1995 | Noel et al. | |
| 5,500,270 A | 3/1996 | Langdon et al. | |
| 5,509,915 A | 4/1996 | Hanson et al. | |
| 5,603,707 A | 2/1997 | Trombetta et al. | |
| 5,614,283 A | 3/1997 | Potnis et al. | |
| 5,635,275 A * | 6/1997 | Biagioli | B29D 99/0089 156/292 |
| 5,643,240 A | 7/1997 | Jackson et al. | |
| 5,846,230 A | 12/1998 | Osborn, III et al. | |
| 5,998,696 A | 12/1999 | Schone | |
| 6,103,953 A | 8/2000 | Cree et al. | |
| 6,228,462 B1 | 5/2001 | Lee et al. | |
| 6,247,914 B1 | 6/2001 | Lindquist et al. | |
| 6,461,716 B1 | 10/2002 | Lee et al. | |
| 6,468,626 B1 | 10/2002 | Takai et al. | |
| 6,627,791 B1 | 9/2003 | Veglio et al. | |
| 6,911,573 B2 | 6/2005 | Chen et al. | |
| 7,518,032 B2 | 4/2009 | Seyler | |
| 7,722,588 B1 | 5/2010 | Johnson et al. | |
| 8,674,171 B2 * | 3/2014 | Seyler | A61F 13/53713 604/378 |
| 2002/0133132 A1 | 9/2002 | Copat et al. | |
| 2004/0013852 A1 | 1/2004 | Curro et al. | |
| 2004/0043189 A1 | 3/2004 | Huang | |
| 2004/0116029 A1 | 6/2004 | Kelly et al. | |
| 2005/0064136 A1 | 3/2005 | Turner et al. | |
| 2005/0118393 A1 | 6/2005 | Corcoran et al. | |
| 2005/0256475 A1 | 11/2005 | Komatsu et al. | |
| 2005/0261649 A1 | 11/2005 | Cohen | |
| 2008/0114317 A1 | 5/2008 | Seyler | |
| 2010/0069867 A1 | 3/2010 | Noda et al. | |

FOREIGN PATENT DOCUMENTS

| | | |
|---|---|---|
| JP | 2002-515354 A | 5/2002 |
| JP | 2002-238947 A | 8/2002 |
| JP | 2008-119447 A | 5/2008 |

* cited by examiner

THREE-DIMENSIONAL APERTURED FILM FOR TRANSMITTING DYNAMICALLY-DEPOSITED AND STATICALLY-RETAINED FLUIDS

CROSS REFERENCE TO RELATED APPLICATIONS

This application is a continuation of U.S. patent application Ser. No. 12/462,565, filed Aug. 4, 2009, now U.S. Pat. No. 8,674,171, which is a continuation-in-part of U.S. application Ser. No. 12/316,323, filed Jan. 29, 2009, now U.S. Pat. No. 8,415,524, which in turn if a continuation of U.S. application Ser. No. 11/559,601, filed Nov. 14, 2006, now U.S. Pat. No. 7,518,032, the disclosures of which are incorporated herein by reference in their entirety.

BACKGROUND OF INVENTION

The present invention relates, generally, to a three-dimensional aperture film for use as a transfer layer in an absorbent article.

Absorbent articles for absorbing body fluids are well known. These articles typically comprise an absorbent core covered by a topsheet, which is positioned adjacent to, and, in use, may contact the user's skin. The topsheet for use in an absorbent article is typically an aperture film, nonwoven, or laminated combinations thereof. Examples of such absorbent articles include diapers, incontinent articles, and sanitary napkins.

One problem associated with absorbent articles is maintaining the dryness of the wearer-facing surface of the topsheet. Generally, when the wearer-facing surface is kept dry, the absorbent article is more comfortable. To maintain a dry wearer-facing surface, the absorbent article should be able to eliminate both dynamically-deposited and statically-retained fluids from the topsheet and transmit them to the absorbent core. Dynamically-deposited fluids are generally voluminous fluids expelled by the user, while statically-retained fluids are residual fluids held in or on the topsheet by surface tension. In addition, the articles need to be able to keep fluids transmitted to the core from migrating back to the wearer-facing side of the article—a phenomenon known as rewet.

Dynamically deposited fluids must be rapidly transmitted to the absorbent core to minimize wearer discomfort and to prevent the lateral run off of fluids leading to leakage and garment soiling. This rapid transmission of dynamically-deposited fluids by the topsheet to the absorbent core is at a rate greater than the absorbent rate of the core. This feature is particularly true with cores that contain significant amounts of superabsorbent polymers. Such polymers have a rate of intake that is inversely proportional to their fluid holding power. Thus, while such polymers have the ability to hold significant amounts of fluids, it is often the case that they take time to fully absorb that fluid. This causes pooling of unabsorbed fluid on the core surface and leads to higher levels of statically-retained fluid over a larger area of the topsheet.

The use of a transfer layer is intended to address these issues. The transfer layer is interposed between the topsheet and the core and serves several main functions. First, the transfer layer provides a void space for fluids to accumulate away from the wearer until they can be absorbed by the core. Secondly, the transfer layer provides a way to laterally disperse the fluids from a saturated area of the core to a less saturated area. Finally, transfer layers made of formed films (as opposed to fibrous nonwoven webs) offer an additional physical barrier between the core and the topsheet and thus help reduce rewet.

SUMMARY OF THE INVENTION

In one embodiment, the disclosure provides a three-dimensional apertured film for use as a transfer layer in an absorbent article. The film has one set of apertures which originate from a continuous surface of the film and a second set of apertures that originate from a discontinuous surface of the film. The apertures in the discontinuous surface comprise at least one large scale aperture, which is capable of transmitting dynamically-deposited fluids through the film by gravity. The discontinuous surface can optionally also include small scale apertures, which are capable of transmitting statically-retained fluids through the film by capillary action. The apertures in the continuous surface can comprise large scale apertures, small scale apertures, or combinations thereof.

In another embodiment, the disclosure provides an absorbent article having a topsheet, an absorbent core, and a transfer layer located between the topsheet and the absorbent core, wherein the acquisition distribution layer comprises a three-dimensional apertured film having one set of apertures which originate from a continuous surface of the film and a second set of apertures that originate from a discontinuous surface of the film. The apertures in the discontinuous surface comprise at least one large scale aperture, which is capable of transmitting dynamically-deposited fluids through the film by gravity. The discontinuous surface can optionally also include small scale apertures, which are capable of transmitting statically-retained fluids through the film by capillary action. The apertures in the continuous surface can comprise large scale apertures, small scale apertures, or combinations thereof.

DETAILED DESCRIPTION

Figure 1:
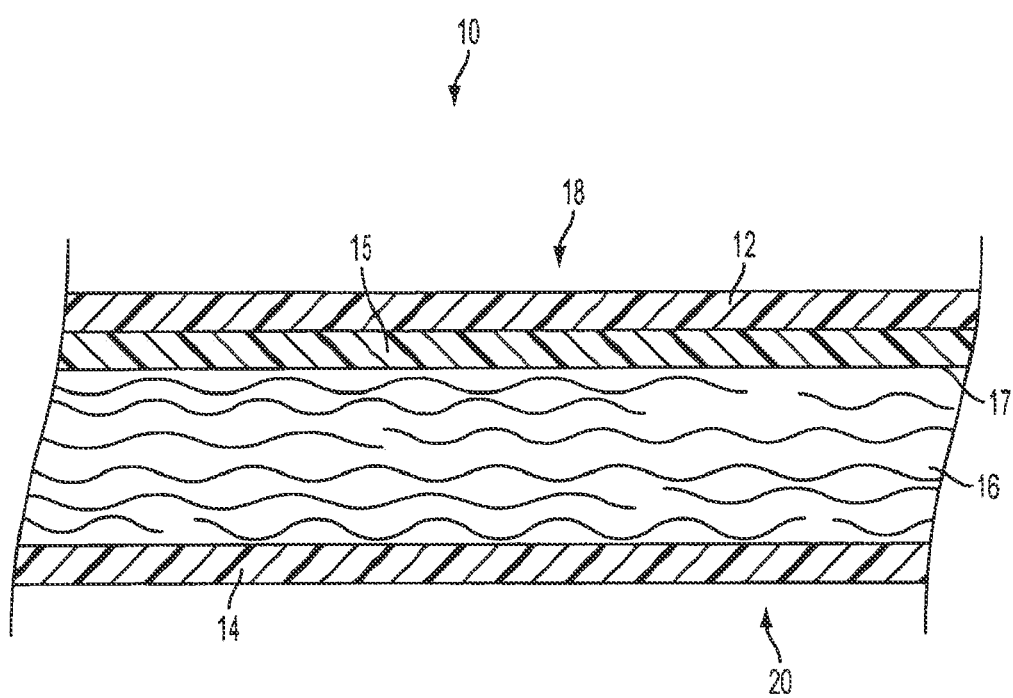
FIG. 1 shows a cross-sectional view of a schematic of an absorbent article in accordance with an embodiment of the disclosure.

Referring to FIG. 1, a simplified representation of a typical absorbent article 10 is shown. The absorbent article 10 basically comprises topsheet 12, acquisition distribution layer 15, absorbent core 16, and a backsheet 14. Other layers may be included in this general construction. Examples of absorbent articles include diapers, incontinent articles, sanitary napkins, and similar articles. It should be understood, however, that FIG. 1 is shown for purposes of example only, and should not be construed to limit the particular type or configuration of absorbent article.

As shown in FIG. 1, the absorbent article 10 has two surfaces, a wearer-facing surface or wearer surface 18 and a garment-facing surface or garment surface 20. The wearer surface 18 is intended to be worn adjacent to the body of the wearer. The garment surface 20 of the absorbent article 10 is on the opposite side and is intended to be placed adjacent to the wearer's undergarments or clothing when the absorbent article 10 is worn.

As can be seen in FIG. 1, when used as a transfer layer for an absorbent article, the three-dimensional film 15 is located beneath the topsheet 12 and adjacent to the top or wearer-facing side 17 of the absorbent core 16. In a preferred embodiment, the topsheet comprises any nonwoven web of individual fibers or threads which are interlaid, but not in any regular, repeating manner. Any nonwoven web commonly known in that art as suitable for topsheet applications can be used. Nonwoven webs have been, in the past, formed by a variety of processes such as, for example, meltblowing processes, spunbonding process, and bonded carded web processes. In lieu of or in addition to a nonwoven web, the topsheet 12 may comprise a three-dimensional film, as is known in the art.

Figure 2:
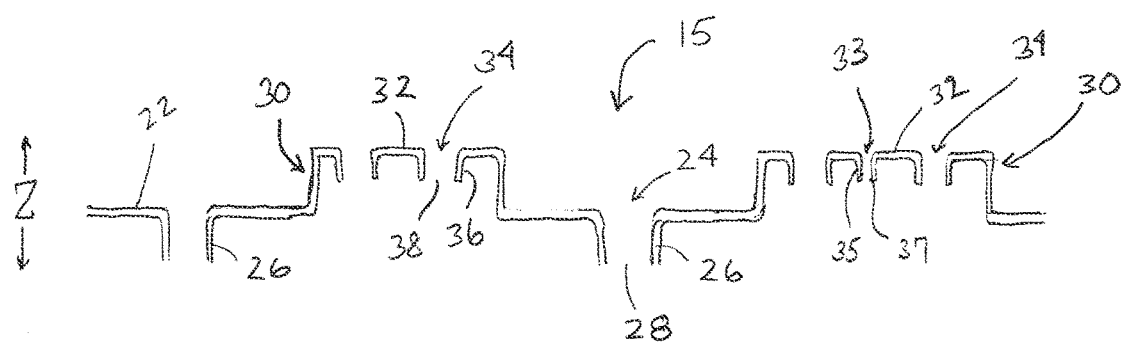
FIG. 2 shows a cross-sectioned view of a three-dimensional apertured film in accordance with an embodiment.

Referring now to FIG. 2, the three-dimensional film 15 comprises a continuous surface 22 with a plurality of drains 24 therein. The term "continuous surface" means that any point on the surface 22 can be reached from any other point on the surface 22 without breaking contact with the surface. The drains 24 are defined by sidewalls 26 that originate in surface 22 and extend downwardly from the surface 22 in a z-direction, terminating in an aperture 28 at the distal end of the sidewalls 26. The z-direction is defined as generally transverse to the plane of the film and is indicated by arrow "Z" in FIGS. 2-4.

The film 15 further comprises protrusions 30 having a top surface 32. The top surfaces 32 collectively comprise a discontinuous surface that is spaced from and generally parallel to the continuous surface 22. The term "discontinuous surface" means that any point on the surface 32 cannot be reached from any other point on the surface 32 without breaking contact with the surface. The top surface of any one protrusion is a continuous surface, but the surfaces 32 of individual protrusions 30 collectively form a discontinuous surface in the film.

A plurality of drains 34 are defined by sidewalls 36 that originate in surface 32 and extend downwardly from the surface 32, terminating in an aperture 38 at the distal end of the sidewalls 36. The drains 34 and sidewalls 36 are thus oriented toward the continuous surface 22 and in the same direction as the apertures 24 and sidewalls 26, but spaced in a different plane. In addition to drains 34, the discontinuous surface 32 may contain capillaries, such as capillary 33. The capillary 33 has the same basic construction as the drains 34 and is defined by sidewalls 35 that originate in the discontinuous surface 32 and extend outwardly therefrom. An aperture 37 is located at the distal end of the sidewalls 35, thus providing fluid communication through the capillary 33.

Figure 3:
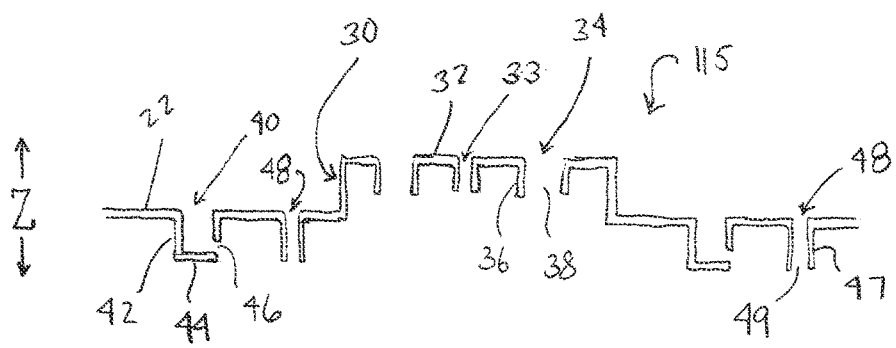
FIG. 3 shows a cross-sectioned view of a three-dimensional apertured film in accordance with an embodiment.

With reference to FIG. 3, the three-dimensional film 115 comprises a continuous surface 22 with a plurality of buckets 40 therein. In this embodiment, the buckets 40 are also defined by sidewalls 42 that originate in the continuous surface 22 and extend downwardly in the z-direction. Buckets 40 further comprise a bottom wall 44 oriented generally parallel to continuous surface 22. At least one of the sidewalls 42 contains an aperture 46 therein. The bottom wall (also referred to as bottom surface) 44 is substantially unapertured. By providing an aperture in the sidewall and leaving the bottom surface substantially intact, the transfer layer 115 can provide fluid management and also provides nearly complete visual occlusion of the absorbent core. The near complete visual occlusion enables an absorbent article with improved masking properties to hide a soiled absorbent core, which is a benefit and desirable property to consumers.

It will be understood that the placement of the aperture 46 is not exact. Nor is the line of demarcation between the bottom surface 44 and the sidewall 42 always well defined. Accordingly, in practice it may be that a portion of bottom surface 44 is apertured, even if most of the aperture 46 is located in the sidewall. For this reason, when we state that the bottom surface 44 is substantially unapertured, we mean that no more than 10% or 12%, preferably no more than 5%, of the surface area of the bottom surface 44 is occupied by the aperture. Similarly, when we state that the aperture 46 is in the sidewall 42, we do not mean to imply that the 100% of the open area is in the sidewall portion.

The embodiments having apertures 46 in the sidewalls 42 allows for better control and flexibility of the z-direction dimension of the film. In particular, unlike the typical apertured three-dimensional formed film, the z-direction dimension of the transfer layer is determined by the depth (i.e., thickness) of the forming screen and not by the diameter of the opening in the screen corresponding to the diameter of the protuberance.

In addition, as seen in FIG. 3, the film 115 contains capillaries 48 that are defined by sidewalls 47 that originate in the continuous surface 22 and extend downwardly therefrom in the z-direction and terminate in an aperture 49 at the distal end of the sidewall 47. Films containing sidewall apertures and capillaries are disclosed in the aforementioned co pending and commonly assigned U.S. application Ser. No. 12/291,427, filed Nov. 10, 2008, the disclosure of which is incorporated herein by reference.

The film 115 of FIG. 3 further comprises protrusions 30 having a top surface 32. As in FIG. 2, the top surfaces 32 collectively comprise a discontinuous surface that is spaced from and generally parallel to the continuous surface 22. A plurality of drains 34 are defined by sidewalls 36 that originate in surface 32 and extend downwardly from the surface 32, terminating in an aperture 38 at the distal end of the sidewalls 36. The drains 34 and sidewalls 36 are thus oriented toward the continuous surface 22 and in the same direction as the drains 24 and sidewalls 26, but spaced in a different plane. As in previous embodiments, the discontinuous surface may also include capillaries, such as capillary 33.

Figure 4:
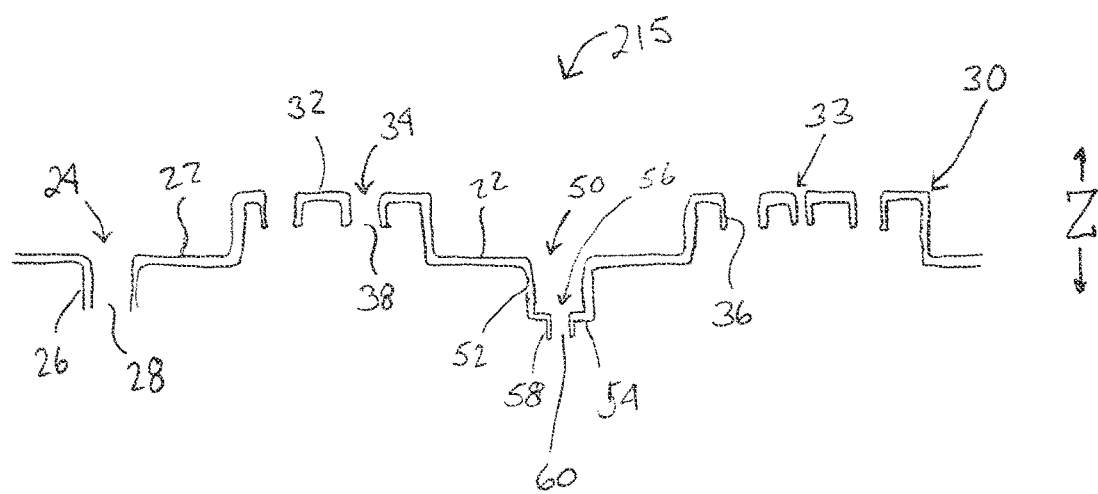
FIG. 4 shows a cross-sectioned view of a three-dimensional apertured film in accordance with an embodiment.

In reference to FIG. 4, the film 215 comprises a continuous surface 22 with a plurality of drains 24 therein. The drains 24 are defined by sidewalls 26 that originate in surface 22 and extend downwardly from the surface 22 in a z-direction, terminating in an aperture 28 at the distal end of the sidewalls 26.

The film 215 of FIG. 4 further comprises protrusions 30 having a top surface 32. The top surfaces 32 collectively comprise a discontinuous surface that is spaced from and generally parallel to the continuous surface 22. A plurality of drains 34 are defined by sidewalls 36 that originate in surface 32 and extend downwardly from the surface 32, terminating in an aperture 38 at the distal end of the sidewalls 36. The drains 34 and sidewalls 36 are thus oriented toward the continuous surface 22 and in the same direction as the apertures 24 and sidewalls 26, but spaced in a different plane. As in previous embodiments, the discontinuous surface may also include capillaries, such as capillary 33.

As also seen in FIG. 4, the film 215 further comprises at least one basin 50 defined by sidewalls 52 that originate in the continuous surface 22 and extend downwardly in the z-direction and bottom wall 54 oriented substantially parallel to the continuous surface 22. The bottom wall 54 contains at least one aperture 56 defined by sidewalls 58 that originate at the bottom wall 54 and extend downwardly. An aperture 60 is located at the distal end of sidewalls 58, permitting fluids collected in basin 50 to pass through the film 215 in the z-direction.

When viewed from above, the shape of the apertures, whether they are drains, capillaries, basins or buckets, may be circular, oval, elliptical, polygonal, or other desired shape. Moreover, the apertures may be arranged in any desired pattern or array and in any desired density or mesh count (i.e., the number of apertures per unit length). A mesh count of 2-25 drains, buckets or basins per linear inch, more preferably 8-20 apertures per linear inch is generally suited for transfer layers in absorbent articles.

In a preferred embodiment, the films transmits dynamically-deposited fluids at a controlled rate using drains in conjunction with basins and/or buckets that are able to collect and temporarily hold fluid before transmitting such fluid to the core. This gives the absorbent core more time to absorb the fluid.

Drains 24, buckets 40 and basins 50 (collectively referred to as "large scale apertures") have diameters which are large enough to allow insult fluids to be acquired through the three-dimensional film by gravity or by application pressure, preferably as rapidly as the fluids are delivered. The capillaries (also called "small scale apertures") 33, 48 are sized such that the capillaries exhibit capillary action and thus are able to transmit fluid in contact with the discontinuous surface 32 or the continuous surface 22.

The protrusions 30 extend upward from the continuous surface 22. In a preferred embodiment, the discontinuous surface 32 of the protrusions 30 will come in contact with the lower surface of the topsheet 12 or extend into the topsheet 12. The number and arrangement of drains 34 and capillaries 33 in the discontinuous surface 32 of the protrusions 30 is not particularly important to the invention and any suitable arrangement, pattern or mesh count may be employed as desired, so long as at least one drain 34 is present. In a preferred embodiment, the protrusions 30 contain 1 to 10 drains, and more preferably 3 to 5 drains. Optionally, each protrusion 30 may contain 1-10 capillaries.

The z-direction dimension or loft of the films may be 400 to 1700 microns, depending on the embodiment. The z-direction distance from the continuous surface 22 of the film to the discontinuous surface 32 of the protrusions 30 can be 50 to 300 microns, more preferably 100 to 250 microns, and most preferably 200 microns. Although FIGS. 2 and 4 illustrate the discontinuous surface 32 of protrusions 30 as being in a common plane, this is not an essential feature. Accordingly, each protrusion 30 may be higher or lower than any other protrusion 30 if desired.

Preferably, the drains and capillaries are tapered whereby their largest diameter is at the opening on the surface 22 or 32. The tapering decreases the likelihood that fluid will be transmitted through the film from the core to the topsheet. The drains, buckets and basins need not be cylindrical in shape to function in their intended manner as long as they are large enough to allow dynamically-deposited fluids to be acquired through the three-dimensional film rapidly. Accordingly, these film structures must be sized and have the proper surface chemistry so that they do not present a barrier for dynamically-deposited fluids. It has been found that diameters greater than 400 microns, more preferably greater than 650 microns, do not present a barrier to fluid flow.

The upper limit of the diameter is determined primarily on aesthetic and on the basis of rewet considerations. That is, larger diameters apertures in the film tends to make the film appear very stiff and harsh, which creates a negative impression with the consumer. Likewise, for larger diameters also create a greater likelihood that fluid can be transmitted from the absorbent core (e.g., upon compression) through the film to the topsheet. In a preferred embodiment, the large scale apertures, such as drains, buckets or basins have diameters preferably no greater than 1200 microns, and more preferably no greater than 1000 microns.

If the apertures, be they drains, basins, buckets or capillaries, do not have a "true" diameter (e.g., they have an oval opening), they should be sized to ensure that they have an equivalent hydraulic diameter (EHD) equal to the respective diameters discussed herein. As used herein, the term equivalent hydraulic diameter is defined by the following equation: EHD=4A/P where A is the area of the irregular aperture and P is the perimeter of the irregular aperture. The equivalent hydraulic diameter is the diameter of a circular aperture having fluid flow characteristics similar to the irregular aperture for which the calculation is being done. See U.S. Pat. No. 4,324,246 which is incorporated herein by reference. Therefore, the term "diameter" as used herein refers to either the apparent diameter or the EHD.

The apertures are preferably irregularly shaped openings randomly distributed in the topsheet. The apertures may be of equal or of different sizes provided that less than about 25 percent of the apertures have a small equivalent hydraulic diameter (EHD).

The capillaries have a smaller diameter such that they do not function appreciably in dynamic situations to transmit significant quantities of rapidly discharged fluid directly to the underlying absorbent core. Rather, the capillaries, if properly sized and positioned, can remove static fluid through the film. The capillaries need to be cylindrical to function in the intended manner. They can be either regular or irregular in shape. The capillaries, however, must be sized and the proper surface chemistry so that they exhibit capillary action. It has been found that capillaries with diameter of less than 375 microns, more preferably less than 250 microns will exhibit capillary action.

In a preferred embodiment, the ratio of the diameter of the smallest of the large aperture structures (i.e., drains, basins and buckets) to that of the diameter of the largest capillary is preferably at least about 2, and more preferably at least about 4. These ratios tend to ensure that the three-dimensional film will effectively transmit dynamically-deposited fluids by gravity and remove static fluid from the topsheet by capillary action.

Preferably, the three-dimensional films are perforated thermoplastic films which have a percent run off of less than about 10 percent and which have an increased liquid flow rate through the tapered drains. Any thermoplastic material which may be formed into flexible film or sheets may be used in the production of the novel film of the present invention. Percent run off is a well known test for absorbent articles that quantifies the ability of the article, or its component parts to acquire liquid. This is measured by a fluid run-off test wherein the test specimen is held at an angle to the horizontal and fluid is applied to the specimen and the amount of fluids that run off the specimen are compared to the amount of fluid that is acquired.

In use, the cover fabric may be wet with baby oil, lotions, etc., from the babies' skin, so the test is also run on a diaper section that has had 1 gram of baby oil (Johnson's Baby Oil) spread evenly over its surface by transfer from a plastic sheet. Stip tensile strength and elongation at break are measured on an Instron Tester at 70° F. and 65 percent relative humidity using 1.0-inch wide samples with a 2-inch distance between jaws and elongating at 50 percent per minute. The results are given in pounds/inches (lb.//in.) for machine direction (MD) and cross direction (XD) as MD/XD.

Exemplary thermoplastic materials include polyesters, polyamides, vinyl polymers and copolymers, e.g., vinyl acetates, vinyl alcohols, vinyl chlorides; poly methacrylates, poly lactic acid, and polyolefins, e.g., polyethylene, polypropylene, and copolymers or blends thereof which may be formed into flexible film or sheet. Particularly preferred perforated films are polyethylene and polypropylene. One suitable material is a polyethylene film having a thickness of from about 20 microns to about 50 microns. Sheets or film made from such materials may contain additives known in the art to achieve the desired physical characteristics.

When using a hydrophobic thermoplastic material such as a polyolefin resin to form the three-dimensional film, the film can be treated to make the film act more hydrophilic. In one embodiment, a migrating or blooming surfactant can be incorporated into the resin mixture prior to extruding the blend to form the film. The migrating surfactant brings more polar moieties to the film surface but they technically don't make the film more polar and therefore wettable. Free surfactants such as those that bloom from a film accomplish wetting not by increasing the surface energy of the film but rather dissolve into the liquid and lower its surface tension to cause wetting. In another embodiment, the film may be exposed to corona treatment after it is formed. Corona treatment introduces ionic species onto the film surface that are bound (at least temporarily) to the surface and they do increase the surface energy of the film. Corona treatment also introduces energy into the film that enhances surfactant migration to the film surface. Such methods are known in the art and are taught, for example by U.S. Pat. Nos. 4,535,020 and 4,456,570, which are incorporated herein by reference. In yet another embodiment, the films may be multilayer films containing a thin, hydrophilic "skin" layer on the wearer topsheet facing surface and the hydrophobic resin blend at the layer furthest from the topsheet. The hydrophilic skin layer may contain a non-migrating surfactant or may be comprised of hydrophilic polymers.

As used herein, the term "hydrophilic" is used to refer to surfaces that are wettable by aqueous fluids (e.g., aqueous body fluids) deposited thereon. Hydrophilicity and wettability are typically defined in terms of contact angle and the surface tension of the fluids and solid surfaces involved. A surface is said to be wetted by an aqueous fluid (hydrophilic) when the fluid tends to spread spontaneously across the surface. Conversely, a surface is considered to be "hydrophobic" if the aqueous fluid does not tend to spread spontaneously across the surface.

The three-dimensional apertured films can be made by a direct melt vacuum formed film (VFF) process. In the case of a direct melt VFF process, a molten web is extruded onto a forming area of a forming screen. A pressure differential applied across the forming screen causes the molten web to conform to the three-dimensional shape of the forming screen to form cells that ultimately rupture at their tips to become apertures. Alternatively, the web may be reheated and partially melted while the web is over the forming area of the forming screen as taught in U.S. Pat. No. 4,151,240. A melted polymer is desirable to form three-dimensional apertures since a melted polymer is more easily pulled into the apertures in a forming screen. The three-dimensional apertured films of the present invention may also be formed by a hydroformed film (HFF) process. In a HFF process, hydraulic pressure in the form of water jets impinges upon a solid web as it crosses the forming area of a forming screen. The force of the high-pressure water causes the web to conform to the three-dimensional shape of the forming screen to form cells that ultimately rupture at their tips to become apertures.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A film, comprising:
a first continuous surface;
a discontinuous surface disposed generally parallel to and spaced from the first continuous surface;
a plurality of first drains formed in the first continuous surface, each of the plurality of first drains being defined by a first sidewall extending downwardly from the first continuous surface and terminating in a first aperture at a distal end of the first sidewall;
a plurality of protrusions extending upwardly from the first continuous surface, each of the plurality of protrusions forming one of a plurality of second continuous surfaces disposed generally parallel to and spaced from the first continuous surface, the plurality of second continuous surfaces collectively forming the discontinuous surface; and
at least one second drain formed in each of the plurality of second continuous surfaces, each of the second drains being defined by a second sidewall extending downwardly from a respective one of the plurality of second continuous surfaces and terminating in a second aperture at a distal end of the second sidewall.

2. The film of claim 1, wherein the plurality of first drains and the at least one second drain are sized to allow insult fluids to be acquired through the film by gravity.

3. The film of claim 2, wherein the plurality of first drains and the at least one second drain have a diameter from 400 microns to 1000 microns.

4. The film of claim 1, further comprising small scale apertures in at least one of the first continuous surface and the discontinuous surface.

5. The film of claim 4, wherein the small scale apertures are sized to allow fluids to be acquired through the film by capillary action.

6. The film of claim 4, wherein the small scale apertures have a diameter less than 375 microns.

7. The film of claim 4, wherein the small scale apertures have a diameter at least 4 times smaller than a diameter of the plurality of first drains and the at least one second drain.

8. The film of claim 1, wherein the plurality of second continuous surfaces are in a common plane.

9. The film of claim 1, wherein the plurality of protrusions extend from 100 to 250 microns above the first continuous surface.

10. An absorbent article comprising a nonwoven fibrous topsheet having an upper and lower surface; an absorbent core; and a film between the topsheet and the absorbent core; the film comprising:
a first continuous surface;
a discontinuous surface disposed generally parallel to and spaced from the first continuous surface;

a plurality of first drains formed in the first continuous surface, each of the plurality first drains being defined by a first sidewall extending downwardly from the first continuous surface and terminating in a first aperture at a distal end of the first sidewall;

a plurality of protrusions extending upwardly from the first continuous surface, each of the protrusions forming one of a plurality of second continuous surfaces disposed generally parallel to and spaced from the first continuous surface, the plurality of second continuous surfaces collectively forming the discontinuous surface; and at least one second drain formed in each of the plurality of second continuous surfaces, each of the second drains being defined by a second sidewall extending downwardly from a respective one of the plurality of second continuous surfaces and terminating in a second aperture at a distal end of the second sidewall.

11. The absorbent article of claim 10, further comprising small scale apertures in at least one of the first continuous and the plurality of second continuous surfaces.

12. The absorbent article of claim 11, wherein the small scale apertures have a diameter at least 4 times smaller than a diameter of the plurality of first drains and the at least one second drain.

13. The absorbent article of claim 10, wherein the plurality of first drains and the at least one second drain have a diameter from 400 microns to 1000 microns.

14. The absorbent article of claim 9, wherein the plurality of second continuous surfaces are in contact with the topsheet.

* * * * *